United States Patent

Burk et al.

(10) Patent No.: US 6,531,504 B2
(45) Date of Patent: Mar. 11, 2003

(54) PROSTANOIC ACID DERIVATIVES AS AGENTS FOR LOWERING INTRAOCULAR PRESSURE

(75) Inventors: Robert M. Burk, Laguna Beach, CA (US); Todd S. Gac, Corona Del Mar, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 09/859,770

(22) Filed: May 17, 2001

(65) Prior Publication Data

US 2002/0177620 A1 Nov. 28, 2002

(51) Int. Cl.$^7$ .................. A61K 31/5575; A61K 31/559
(52) U.S. Cl. .............. 514/438; 514/443; 514/530; 514/569
(58) Field of Search .................. 514/438, 443, 514/530, 569

(56) References Cited

U.S. PATENT DOCUMENTS

| | | | |
|---|---|---|---|
| 4,994,274 A | 2/1991 | Chan et al. | |
| 5,028,624 A | 7/1991 | Gluchowski et al. | |
| 5,034,413 A | 7/1991 | Chan et al. | |
| 5,446,041 A | 8/1995 | Chan et al. | |
| 6,310,087 B2 * | 10/2001 | Burk ..................... | 514/438 |

OTHER PUBLICATIONS

Bito, L.Z., *Biological Protection with Prostaglandins*, Cohen, M. M., ed., Boca Raton, Fla, CRC Press Inc., 1985, pp. 231–252.
Bito, L.Z., *Applied Pharmacology in the Medical Treatment of Glaucomas*, Drance, S.M. and Neufeld, A.H. eds, New York, Grune & Stratton, 1984, pp. 477–505.
Nilsson et al, Invest. Opthalmol. Vis. Sci. (suppl), 284 (1987).
Bito. L.Z., Arch. Ophthalmol. 105, 1036 (1987).
Siebold et al, Prodrug 5 3 1989.

* cited by examiner

*Primary Examiner*—Robert Gerstl
(74) *Attorney, Agent, or Firm*—Robert J. Baran; Martin A. Voet; Carlos A. Fisher

(57) ABSTRACT

The present invention provides a method of treating ocular hypertension or glaucoma which comprises administering to an animal having ocular hypertension or glaucoma therapeutically effective amount of a compound represented by the general formula I;

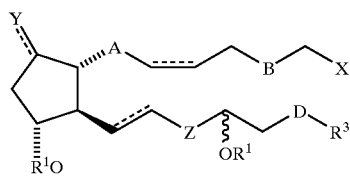

Figure 1:
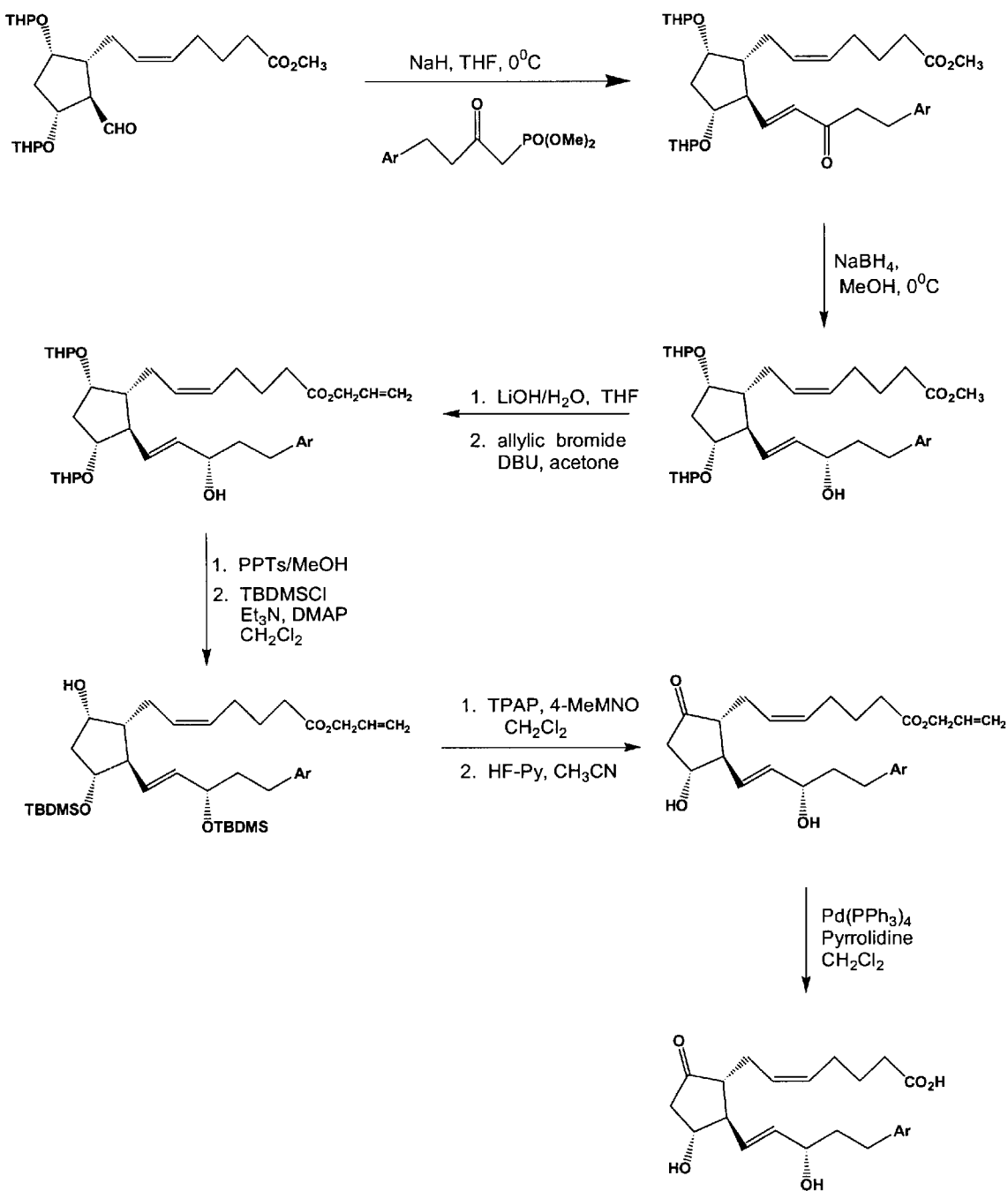

wherein hatched lines represent the α configuration, a triangle represents the β configuration and a dotted line represents the presence or absence of a double bond;

A and B are $CH_2$;

D represents a covalent bond or $CH_2$, O, S or NH;

X is $CO_2R$, $CONR_2$, $CH_2OR$, $P(O)(OR)_2$, $CONRSO_2R$ $SONR_2$ or

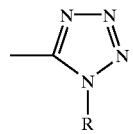

Y is O, OH, $OCOR^2$, halogen or cyano;

Z is $CH_2$ or a covalent bond;

R is H or $R^2$;

$R^1$ is H, $R^2$, phenyl, or $COR^2$;

$R^2$ is $C_1$–$C_5$ lower alkyl or alkenyl and $R_3$ is benzothienyl, benzofuranyl, naphthyl or substituted derivatives thereof, wherein the substituents maybe selected from the group consisting of $C_1$–$C_5$ alkyl, halogen, $CF_3$, CN, $NO_2$, $NR_2$, $CO_2R$ and OR.

3 Claims, 1 Drawing Sheet

PROSTANOIC ACID DERIVATIVES AS AGENTS FOR LOWERING INTRAOCULAR PRESSURE

FIELD OF THE INVENTION

The present invention relates to prostanoic acid derivatives as potent ocular hypotensives that are particularly suited for the management of glaucoma.

BACKGROUND OF THE INVENTION

Description of Related Art

Ocular hypotensive agents are useful in the treatment of a number of various ocular hypertensive conditions, such as post-surgical and post-laser trabeculectomy ocular hypertensive episodes, glaucoma, and as presurgical adjuncts.

Glaucoma is a disease of the eye characterized by increased intraocular pressure. On the basis of its etiology, glaucoma has been classified as primary or secondary. For example, primary glaucoma in adults (congenital glaucoma) may be either open-angle or acute or chronic angle-closure. Secondary glaucoma results from pre-existing ocular diseases such as uveitis, intraocular tumor or an enlarged cataract.

The underlying causes of primary glaucoma are not yet known. The increased intraocular tension is due to the obstruction of aqueous humor outflow. In chronic open-angle glaucoma, the anterior chamber and its anatomic structures appear normal, but drainage of the aqueous humor is impeded. In acute or chronic angle-closure glaucoma, the anterior chamber is shallow, the filtration angle is narrowed, and the iris may obstruct the trabecular meshwork at the entrance of the canal of Schlemm. Dilation of the pupil may push the root of the iris forward against the angle, and may produce pupilary block and thus precipitate an acute attack. Eyes with narrow anterior chamber angles are predisposed to acute angle-closure glaucoma attacks of various degrees of severity.

Secondary glaucoma is caused by any interference with the flow of aqueous humor from the posterior chamber into the anterior chamber and subsequently, into the canal of Schlemm. Inflammatory disease of the anterior segment may prevent aqueous escape by causing complete posterior synechia in iris bombe, and may plug the drainage channel with exudates. Other common causes are intraocular tumors, enlarged cataracts, central retinal vein occlusion, trauma to the eye, operative procedures and intraocular hemorrhage.

Considering all types together, glaucoma occurs in about 2% of all persons over the age of 40 and may be asymptotic for years before progressing to rapid loss of vision. In cases where surgery is not indicated, topical b-adrenoreceptor antagonists have traditionally been the drugs of choice for treating glaucoma.

Certain eicosanoids and their derivatives have been reported to possess ocular hypotensive activity, and have been recommended for use in glaucoma management. Eicosanoids and derivatives include numerous biologically important compounds such as prostaglandins and their derivatives. Prostaglandins can be described as derivatives of prostanoic acid which have the following structural formula:

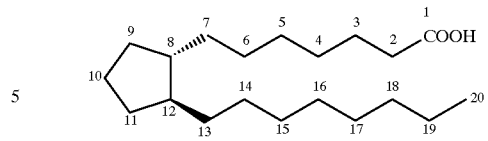

Various types of prostaglandins are known, depending on the structure and substituents carried on the alicyclic ring of the prostanoic acid skeleton. Further classification is based on the number of unsaturated bonds in the side chain indicated by numerical subscripts after the generic type of prostaglandin [e.g. prostaglandin $E_1$ ($PGE_1$), prostaglandin $E_2$ ($PGE_2$)], and on the configuration of the substituents on the alicyclic ring indicated by $\alpha$ or $\beta$ [e.g. prostaglandin $F_{2\alpha}$ ($PGF_{2\beta}$)].

Prostaglandins were earlier regarded as potent ocular hypertensives, however, evidence accumulated in the last decade shows that some prostaglandins are highly effective ocular hypotensive agents, and are ideally suited for the long-term medical management of glaucoma (see, for example, Bito, L. Z. *Biological Protection with Prostaglandins,* Cohen, M. M., ed., Boca Raton, Fla., CRC Press Inc., 1985, pp. 231–252; and Bito, L. Z., *Applied Pharmacology in the Medical Treatment of Glaucomas* Drance, S. M. and Neufeld, A. H. eds., New York, Grune & Stratton, 1984, pp. 477–505. Such prostaglandins include $PGF_{2\alpha}$, $PGF_{1\alpha}$, $PGE_2$, and certain lipid-soluble esters, such as $C_1$ to $C_2$ alkyl esters, e.g. 1-isopropyl ester, of such compounds.

Although the precise mechanism is not yet known experimental results indicate that the prostaglandin-induced reduction in intraocular pressure results from increased uveoscleral outflow [Nilsson et.al., *Invest. Ophthalmol. Vis. Sci.* (suppl), 284 (1987)].

The isopropyl ester of $PGF_{2\alpha}$ has been shown to have significantly greater hypotensive potency than the parent compound, presumably as a result of its more effective penetration through the cornea. In 1987, this compound was described as "the most potent ocular hypotensive agent ever reported" [see, for example, Bito, L. Z., *Arch. Ophthalmol.* 105, 1036 (1987), and Siebold et.al., *Prodrug* 53 (1989)].

Whereas prostaglandins appear to be devoid of significant intraocular side effects, ocular surface (conjunctival) hyperemia and foreign-body sensation have been consistently associated with the topical ocular use of such compounds, in particular $PGF_{2\alpha}$ and its prodrugs, e.g., its 1-isopropyl ester, in humans. The clinical potentials of prostaglandins in the management of conditions associated with increased ocular pressure, e.g. glaucoma are greatly limited by these side effects.

In a series of co-pending United States patent applications assigned to Allergan, Inc. prostaglandin esters with increased ocular hypotensive activity accompanied with no or substantially reduced side-effects are disclosed. The co-pending U.S. Ser. No. 596,430 (filed Oct. 10, 1990, now U.S. Pat. No. 5,446,041), relates to certain 11-acyl-prostaglandins, such as 11-pivaloyl, 11-acetyl, 11-isobutyryl, 11-valeryl, and 11-isovaleryl $PGF_{2\alpha}$. Intraocular pressure reducing 15-acyl prostaglandins are disclosed in the co-pending application U.S. Ser. No. 175, 476 (filed Dec. 29, 1993). Similarly, 11,15-9,15 and 9,11-diesters of prostaglandins, for example 11,15-dipivaloyl $PGF_{2\alpha}$ are known to have ocular hypotensive activity. See the co-pending patent applications U.S. Ser. No. 385,645

(filed Jul. 7, 1989, now U.S. Pat. No. 4,994,274), Ser. No. 584,370 (filed Sep. 18, 1990, now U.S. Pat. No. 5,028,624) and Ser. No. 585,284 (filed Sep. 18, 1990, now U.S. Pat. No. 5,034,413). The disclosures of all of these patent applications are hereby expressly incorporated by reference.

SUMMARY OF THE INVENTION

The present invention concerns a method of treating ocular hypertension which comprises administering to a mammal having ocular hypertension a therapeutically effective amount of a compound of formula I

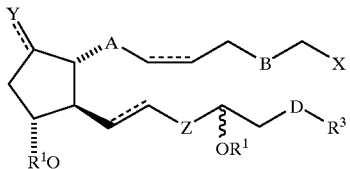

wherein hatched lines represent the α configuration, a triangle represents the β configuration, a wavy line represents either the α configuration or the β configuration, and a dotted line represents the presence or absence of a double bond;

A and B are $CH_2$;

D represents a covalent bond or $CH_2$, O, S or NH;

X is $CO_2R$, $CONR_2$, $CH_2OR$, $P(O)(OR)_2$, $CONRSO_2R$, $SONR_2$ or

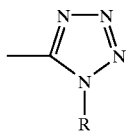

Y is O, OH, $OCOR^2$, halogen or cyano;

Z is $CH_2$ or a covalent bond;

R is H or $R^2$;

$R^1$ is H, $R^2$, phenyl, or $COR_2$;

$R^2$ is $C_1$–$C_5$ lower alkyl or alkenyl and $R^3$ is benzothienyl, benzofuranyl, naphthyl, or substituted derivatives thereof, wherein the substituents maybe selected from the group consisting of $C_1$–$C_5$ alkyl, halogen, $CF_3$, CN, $NO_2$, $NR_2$, $CO_2R$ and OR.

In a still further aspect, the present invention relates to a pharmaceutical product, comprising a container adapted to dispense its contents in a metered form; and an ophthalmic solution therein, as hereinabove defined.

Finally, certain of the compounds represented by the above formula, disclosed below and utilized in the method of the present invention are novel and unobvious.

BRIEF DESCRIPTION OF THE DRAWING FIGURES

FIG. 1 is a schematic of the chemical synthesis of a certain compounds of the invention as disclosed in Examples 1 and 2.

DETAILED DESCRIPTION OF THE INVENTION

The present invention relates to the use of prostanoic acid derivatives as ocular hypotensives. The compounds used in accordance with the present invention are encompassed by the following structural formula I:

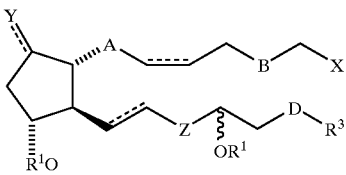

A preferred group of the compounds of the present invention includes compounds that have the following structural formula II:

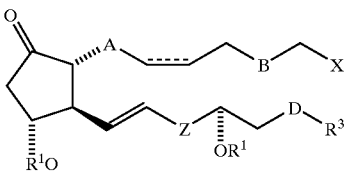

Another preferred group includes compounds having the formula III:

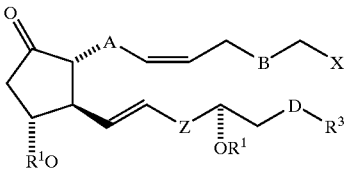

In the above formulae, the substituents and symbols are as hereinabove defined.

In the above formulae:

Preferably D represents a covalent bond or is $CH_2$; more preferably D is $CH_2$.

Preferably Z represents a covalent bond.

Preferably R is H.

Preferably $R^1$ is H.

Preferably Y=O.

Preferably X is $CO_2R$ and more preferably R is selected from the group consisting of H, methyl, i-propyl and n-propenyl.

The above compounds of the present invention may be prepared by methods that are known in the art or according to the working examples below. The compounds, below, are especially preferred representative, of the compounds of the present invention.

(Z)-7-{(1R,2R,3R)-2-[(E)-(S)-5-(3-Chlorobenzo[b]thiophen-2-yl)-3-hydroxypent-1-enyl]-3-hydroxy-5-oxocyclopentyl}hept-5-enoic acid allyl ester (6a)

(Z)-7-{(1 R,2R,3R)-2-[(E)-(S)-5-(3-Chlorobenzo[b]thiophen-2-yl)-3-hydroxypent-1-enyl]-3-hydroxy-5-oxocyclopentyl}hept-5-enoic acid (7a)

(Z)-7-{(1R,2R,3R)-2-((E)-(S)-5-Benzo[b]thiophen-2-yl-3-hydroxypent-1-enyl]-3-hydroxy-5-oxocyclopentyl}hept-5-enoic acid allyl ester (6b)

(Z)-7-{(1R,2R,3R)-2-((E)-(S)-5-Benzo[b]thiophen-2-yl-3-hydroxypent-1-enyl]-3-hydroxy-5-oxocyclopentyl}hept-5-enoic acid (7b)

(Z)-7-{(1R,2R,3R)-3-Hydroxy-2-((E)-(S)-3-hydroxy-5-naphthalen-2-yl-pent-1-enyl)-5-oxocyclopentyl}hept-5-enoic acid allyl ester (6c)

(Z)-7-{(1R,2R,3R)-3-Hydroxy-2-((E)-(S)-3-hydroxy-5-naphthalen-2-yl-pent-1-enyl)-5-oxocyclopentyl}hept-5-enoic acid (7c)

(Z)-7-{(1R,2R,3R)-2-[(E)-(S)-5-(4-Bromo-2,5-dimethylthiophen-3-yl)-3-hydroxypent-1-enyl]-3-hydroxy-5-oxocyclopentyl}hept-5-enoic acid allyl ester 6d)

(Z)-7-{(1R,2R,3R)-2-[(E)-(S)-5-(4-Bromo-2,5-dimethylthiophen-3-yl)-3-hydroxypent-1-enyl]-3-hydroxy-5-oxocyclopentyl}hept-5-enoic acid (7d)

Pharmaceutical compositions may be prepared by combining a therapeutically effective amount of at least one compound according to the present invention, or a pharmaceutically acceptable acid addition salt thereof as an active ingredient, with conventional ophthalmically acceptable pharmaceutical excipients, and by preparation of unit dosage forms suitable for topical ocular use. The therapeutically efficient amount typically is between about 0.0001 and about 5% (w/v), preferably about 0.001 to about 1.0% (w/v) in liquid formulations.

For ophthalmic application, preferably solutions are prepared using a physiological saline solution as a major vehicle. The pH of such ophthalmic solutions should preferably be maintained between 6.5 and 7.2 with an appropriate buffer system. The formulations may also contain conventional, pharmaceutically acceptable preservatives, stabilizers and surfactants.

Preferred preservatives that may be used in the pharmaceutical compositions of the present invention include, but are not limited to, benzalkonium chloride, chlorobutanol, thimerosal, phenylmercuric acetate and phenylmercuric nitrate. A preferred surfactant is, for example, Tween 80. Likewise, various preferred vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In a similar vein, an ophthalmically acceptable antioxidant for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. The preferred chelating agent is edentate disodium, although other chelating agents may also be used in place or in conjunction with it.

The ingredients are usually used in the following amounts:

| Ingredient | Amount (% w/v) |
|---|---|
| active ingredient | about 0.001–5 |
| preservative | 0–0.10 |

| Ingredient | Amount (% w/v) |
|---|---|
| vehicle | 0–40 |
| tonicity adjustor | 1–10 |
| buffer | 0.01–10 |
| pH adjustor | q.s. pH 4.5–7.5 |
| antioxidant | as needed |
| surfactant | as needed |
| purified water | as needed to make 100% |

The actual dose of the active compounds of the present invention depends on the specific compound, and on the condition to be treated; the selection of the appropriate dose is well within the knowledge of the skilled artisan.

The ophthalmic formulations of the present invention are conveniently packaged in forms suitable for metered application, such as in containers equipped with a dropper, to facilitate the application to the eye. Containers suitable for dropwise application are usually made of suitable inert, non-toxic plastic material, and generally contain between about 0.5 and about 15 ml solution.

The invention is further illustrated by the following non-limiting Examples, which are summarized in the reaction schemes of figures 1 through 3 wherein the compounds are identified by the same designator in both the Examples and the Figures.

EXAMPLE 1

(Z)-7-{(1R,2R,3R,5S)-2-[(E)-(S)-5-(3-Chlorobenzo[b]thiophen-2-yl)-3-hydroxypent-1-enyl]-3-hydroxy-5-oxocyclopentyl}hept-5-enoic Acid Allyl Ester (6a)

Step 1: Preparation of Enone (2a)

To a suspension of sodium hydride (39 mg, 1.7 mmol) in tetrahydrofuran (THF) (3.1 mL) cooled to 0 ° C. was added [4-(3-chlorobenzo[b]thiophen-2-yl)-2-oxobutyl]phosphonic acid dimethyl ester (536 mg, 1.7 mmol) in THF (2.0 mL). After 15 minutes a solution of aldehyde 1 (750 mg, 1.54 mmol) in THF (3.0 mL) was added and the reaction solution was allowed to slowly warm to 23° C. over a period of 16 h. The reaction was quenched with saturated aqueous $NH_4Cl$ and extracted with ethylacetate (EtOAc). The combined organics were washed with brine, dried over $MgSO_4$, filtered and concentrated in vacuo. Purification of the residue by flash column chromatography (FCC) (silica gel, 3:2 hexane/EtOAc) provided 1.0 g (98%) of enone 2a.

Step 2: Preparation of α-alcohol (3a)

Sodium tetrahydridoborate (57 mg, 1.51 mmol) was added to a solution of enone 2a in MeOH (3.1 mL) at 0° C. After 4 h the solvent was removed in vacuo and the residue was partitioned between saturated aqueous ammonium chloride and $CH_2Cl_2$. The organic portion was separated, dried ($Na_2SO_4$), filtered and concentrated in vacuo. Purification of the residue by flash column chromatography (silica gel, 3:2 hexane/EtOAc) afforded 500 mg (50%) of pure α-alcohol 3a.

Step 3: Preparation of Allyl Ester (4a)

Lithium hydroxide (3.5 mL of a 0.5N solution in $H_2O$, 1.74 mmol) was added to a solution of the ester 3a (500 mg, 0.76 mmol) in THF (7.0 mL) at 23° C. After 16 h the reaction mixture was acidified with 1N HCl and extracted with EtOAc. The organic portion was washed twice with brine, dried over $Na_2SO_4$, filtered and concentrated in vacuo. The residue was purified by flash column chromatography (silica gel, 100% EtOAc) to afford 339 mg (70%) of the corresponding free acid.

A solution of the acid in acetone (1.1 mL) was treated with 1,8-diazabicyclo[5.4.0]undec-7-ene (0.24 mL, 1.57 mmol) followed by allylbromide (0.23 mL, 2.62 mmol) and stirred at 23° C. for 16 h. The solvent was removed in vacuo. The residue was diluted with EtOAc and washed with 1N HCl, saturated aqueous $NaHCO_3$ and brine. The organic portion was dried ($MgSO_4$), filtered and concentrated in vacuo. Purication of the residue by flash column chromatography gave 293 mg (81%) of the allyl ester 4a.

Step 4: Preparation of bis-TBDMS Ether (5a)

A solution of bis-THP ether 4a (293 mg, 0.43 mmol) and pyridinium p-toluene sulfonate (129 mg, 0.51 mmol) in MeOH (0.85 mL) was heated at 40° C. for 16 h. The solvent was removed in vacuo. The residue was diluted with EtOAc and then washed with 1N HCl, saturated aqueous $NaHCO_3$, and brine. The organic portion was dried over $MgSO_4$, filtered and concentrated in vacuo. Purification of the residue by flash chromatography (silica gel, 100% EtOAc) gave 217 mg (98%) of the corresponding trihydroxy-ester.

A solution of the trihydroxy-ester, TBDMSCl (129 mg, 0.86 mmol), 4-dimethylaminopyridine (12.8 mg, 0.10 mmol) and $Et_3N$ (0.18 mL, 1.25 mmol) in $CH_2Cl_2$ (0.84 mL) was stirred for 16 h. The reaction was diluted with EtOAc and washed with 1N HCl, saturated aqueous $NaHCO_3$, and brine. The organic portion was dried over $MgSO_4$, filtered and concentrated in vacuo. Purification of the residue by flash chromatography (silica gel, 4:1 hex/EtOAc) gave 178 mg (57%) of the bis-TBDMS ether 5a.

Step 5: Oxidation and Deprotection of (5a)

Tetrapropylammonium perruthenate (4.2 mg, 0.012 mmol) was added to a mixture of alcohol 5a (178 mg, 0.24 mmol), 4-methylmorpholine N-oxide (42 mg, 0.36 mmol) and crushed 4A sieves (10 mg) in CH2Cl2 (0.5 mL) at 23° C. After 4 h the reaction was concentrated in vacuo and the residue was purified by flash column chromatography (silica gel, 4:1 hex/EtOAc) to afford 160 mg (90%) of the corresponding 9-keto ester.

The 9-keto ester was deprotected with hydrogen fluoride-pyridine (0.23 mL) in $CH_3CN$ (7.2 mL) for 18 h. The reaction was neutralized with $NaHCO_3$ and extracted with EtOAc. The organic portion was washed with brine, dried ($MgSO_4$), filtered and concentrated in vacuo. The residue was purified by flash column chromatography (silica gel, 3:1 hex/EtOAc) to yield 94 mg (85%) of allyl ester 6a.

EXAMPLE 2

(Z)-7-{(1R,2R,3R,5S)-2-[(E)-(S)-5-(3-Chlorobenzo [b]thiophen-2-yl)-3-hydroxypent-1-enyl]-3-hydroxy-5-oxocyclopentyl}hept-5-enoic Acid (7a)

Pyrrolidine (15 mL, 0.178 mmol) was added to a solution of allyl ester 7a (46 mg, 0.089 mmol) and tetrakis (triphenylphosphine)palladium(0) (10.3 mg, 0.009 mmol) in $CH_2Cl_2$ (0.2 mL) at 23° C. After 4 h the reaction was diluted with EtOAc and washed with 1N HCl then brine. The organic portion was dried ($MgSO_4$), filtered and concentrated in vacuo. Purification of the residue by flash column chromatography (silica gel, 9:1 $CH_2Cl_2$/MeOH) gave 10 mg (24%) of the above titled compound.

The effects of the compounds of this invention on intraocular pressure are also measured. The compounds are prepared at the said concentrations in a vehicle comprising 0.1% polysorbate 80 and 10 mM TRIS base. Dogs are treated by administering 25 μl to the ocular surface, the contralateral eye received vehicle as a control. Intraocular pressure is measured by applanation pneumatonometry. Dog intraocular pressure is measured immediately before drug administration and at 6 hours thereafter.

Compounds 6(a) and 7(a) are examined and show a pronounced ocular hypotensive effect in dogs and the glaucomatous cynomonlgus monkeys, respectively.

The foregoing description details specific methods and compositions that can be employed to practice the present invention, and represents the best mode contemplated. However, it is apparent for one of ordinary skill in the art that further compounds with the desired pharmacological properties can be prepared in an analogous manner, and that the disclosed compounds can also be obtained from different starting compounds via different chemical reactions. Similarly, different pharmaceutical compositions may be prepared and used with substantially the same result. Thus, however detailed the foregoing may appear in text, it should not be construed as limiting the overall scope hereof, rather, the ambit of the present invention is to be governed only by the lawful construction of the appended claims.

What is claimed is:

1. A method of treating ocular hypertension or glaucoma which comprises administering to an animal having ocular hypertension or glaucoma a compound selected from the group consisting of (Z)-7-{(1R,2R,3R)-2-[(E)-(S)-5-(3-Chlorobenzo[b] thiophen-2-yl)-3-hydroxypent-1-enyl]-3-hydroxy-5-oxocyclopentyl}hept-5-enoic acid allyl ester (6a)

(Z)-7-{(1R,2R,3R)-2-[(E)-(S)-5-(3-Chlorobenzo[b] thiophen-2-yl)-3-hydroxypent-1-enyl]-3-hydroxy-5-oxocyclopentyl}hept-5-enoic acid (7a)

(Z)-7-{(1R,2R,3R)-2-((E)-(S)-5-Benzo[b]thiophen-2-yl-3-hydroxypent-1-enyl]-3-hydroxy-5-oxocyclopentyl}hept-5-enoic acid allyl ester (6b)

(Z)-7-{(1R,2R,3R) 2-((E)-(S)-5-Benzo[b]thiophen-2-yl-3-hydroxypent-1-enyl]-3-hydroxy-5-oxocyclopentyl}hept-5-enoic acid (7b)

(Z)-7-{(1R,2R,3R)-3-Hydroxy-2-((E)-(S)-3-hydroxy-5-naphthalen-2-yl-pent-1-enyl)-5-oxocyclopentyl}hept-5-enoic acid allyl ester (6c)

(Z)-7-{(1R,2R,3R)-3-Hydroxy-2-((E)-(S)-3-hydroxy-5-naphthalen-2-yl-pent-1-enyl)-5-oxocyclopentyl}hept-5-enoic acid (7c)

(Z)-7-{(1R,2R,3R)-2-[(E)-(S)-5-(4-Bromo-2,5-dimethylthiophen-3-yl)-3-hydroxypent-1-enyl]-3-hydroxy-5-oxocyclopentyl}hept-5-enoic acid allyl ester (6d) and (Z)-7-{(1R,2R,3R)-2-[(E)-(S)-5-(4-Bromo-2,5-dimethylthiophen-3-yl)-3-hydroxypent-1-enyl]-3-hydroxy-5-oxocyclopentyl}hept-5-enoic acid (7d).

2. An ophthalmic solution comprising a therapeutically effective amount of a compound selected from the group consisting of (Z)-7-{(1R,2R,3R)-2-[(E)-(S)-5-(3-Chlorobenzo[b] thiophen-2-yl)-3-hydroxypent-1-enyl]-3-hydroxy-5-oxocyclopentyl}hept-5-enoic acid allyl ester (6a)

(Z)-7-{(1R,2R,3R)-2-[(E)-(S)-5-(3-Chlorobenzo[b] thiophen-2-yl)-3-hydroxypent-1-enyl]-3-hydroxy-5-oxocyclopentyl}hept-5-enoic acid (7a)

(Z)-7-{(1R,2R,3R)-2-((E)-(S)-5-Benzo[b]thiophen-2-yl-3-hydroxypent-1-enyl]-3-hydroxy-5-oxocyclopentyl}hept-5-enoic acid allyl ester (6b)

(Z)-7-{(1R,2R,3R) 2-((E)-(S)-5-Benzo[b]thiophen-2-yl-3-hydroxypent-1-enyl]-3-hydroxy-5-oxocyclopentyl}hept-5-enoic acid (7b)

(Z)-7-{(1R,2R,3R)-3-Hydroxy-2-((E)-(S)-3-hydroxy-5-naphthalen-2-yl-pent-1-enyl)-5-oxocyclopentyl}hept-5-enoic acid allyl ester (6c)

(Z)-7-{(1R,2R,3R)-3-Hydroxy-2-((E)-(S)-3-hydroxy-5-naphthalen-2-yl-pent-1-enyl)-5-oxocyclopentyl}hept-5-enoic acid (7c)

(Z)-7-{(1R,2R,3R)-2-[(E)-(S)-5-(4-Bromo-2,5-dimethylthiophen-3-yl)-3-hydroxypent-1-enyl]-3- hydroxy-5-oxocyclopentyl}hept-5-enoic acid allyl ester (6d) and (Z)-7-{(1R,2R,3R)-2-[(E)-(S)-5-(4-Bromo-2,5-dimethylthiophen-3-yl)-3-hydroxypent-1-enyl]-3-hydroxy-5-oxocyclopentyl}hept-5-enoic acid (7d).

3. A pharmaceutical product, comprising a container adapted to dispense the contents of said container in metered form; and an ophthalmic solution according to claim 2 in said container.

* * * * *